US010722469B2

(12) United States Patent
Lu et al.

(10) Patent No.: US 10,722,469 B2
(45) Date of Patent: Jul. 28, 2020

(54) METHOD FOR PREPARING PHARMACEUTICAL COMPOSITION COMPRISING QUINOLINE DERIVATIVE OR SALT THEREOF

(71) Applicant: Jiangsu Hengrui Medicine Co., Ltd., Lianyungang, Jiangsu (CN)

(72) Inventors: Yun Lu, Jiangsu (CN); Xinhua Zhang, Jiangsu (CN); Chenyang Wang, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/071,572

(22) PCT Filed: Jan. 23, 2017

(86) PCT No.: PCT/CN2017/072156
§ 371 (c)(1),
(2) Date: Jul. 20, 2018

(87) PCT Pub. No.: WO2017/129088
PCT Pub. Date: Aug. 3, 2017

(65) Prior Publication Data
US 2019/0054025 A1  Feb. 21, 2019

(30) Foreign Application Priority Data
Jan. 27, 2016 (CN) .......................... 2016 1 0057228

(51) Int. Cl.
*A61K 9/16* (2006.01)
*A61K 31/4709* (2006.01)
(Continued)

(52) U.S. Cl.
CPC .......... *A61K 9/1694* (2013.01); *A61K 9/1611* (2013.01); *A61K 9/1617* (2013.01);
(Continued)

(58) Field of Classification Search
None
See application file for complete search history.

(56) References Cited

U.S. PATENT DOCUMENTS

2003/0190365 A1* 10/2003 Fergione ............ A61K 31/7052
424/489
2006/0039968 A1* 2/2006 Manikandan ........ A61K 9/2027
424/464
(Continued)

FOREIGN PATENT DOCUMENTS

CN     101824029 A     9/2010
CN     102675287 A     9/2012
(Continued)

OTHER PUBLICATIONS

X Zhu, L Li, G Zhang, H Wan, C Yang, X Diao, X Chen, L Zhang, D Zhong. "Metabolic characterization of pyrotinib in humans by ultra-performance liquid chromatography/quadrupole time-of-flight mass spectrometry." Journal of Chromatography B, vol. 1033-1034, 2016, pp. 117-127. (Year: 2016).*
(Continued)

*Primary Examiner* — Isaac Shomer
(74) *Attorney, Agent, or Firm* — Ice Miller LLP

(57) ABSTRACT

The present invention provides a method for preparing a pharmaceutical composition containing a quinoline derivative or a salt thereof. Specifically, the invention provides a method for preparing a pharmaceutical composition containing (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmaceutically acceptable salt thereof. The method uses a wetting agent containing at least one organic solvent for a wet granulation in a preparation process of the pharmaceutical composition. The pharmaceutical composition prepared using the method
(Continued)

has a uniform distribution of grain sizes during the preparation process and a property of rapid and uniform dissolution.

4 Claims, 3 Drawing Sheets

(51) Int. Cl.
    *A61K 47/38*     (2006.01)
    *A61K 9/48*     (2006.01)
    *A61K 9/20*     (2006.01)

(52) U.S. Cl.
    CPC .......... *A61K 9/1623* (2013.01); *A61K 9/1635* (2013.01); *A61K 9/1652* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/48* (2013.01); *A61K 9/485* (2013.01); *A61K 9/4833* (2013.01); *A61K 9/4858* (2013.01); *A61K 9/4866* (2013.01); *A61K 31/4709* (2013.01); *A61K 47/38* (2013.01)

(56) References Cited

U.S. PATENT DOCUMENTS

| | | | | |
|---|---|---|---|---|
| 2006/0057073 A1* | 3/2006 | Lintz | .................... | A61K 9/1611 424/45 |
| 2012/0165352 A1* | 6/2012 | Tang | .................... | C07D 401/12 514/266.21 |
| 2013/0150386 A1* | 6/2013 | Goodenow | ............ | A61K 45/06 514/266.4 |
| 2013/0338190 A1* | 12/2013 | Li | ...................... | A61K 31/4709 514/313 |
| 2015/0166511 A1* | 6/2015 | Sun | ...................... | C07D 401/14 514/313 |
| 2016/0221987 A1* | 8/2016 | DeCrescenzo | ..... | A61K 31/4439 |

FOREIGN PATENT DOCUMENTS

| | | |
|---|---|---|
| CN | 102471312 B | 6/2014 |
| CN | 102933574 B | 10/2014 |
| CN | 103974949 B | 11/2015 |

OTHER PUBLICATIONS

Ha Lieberman, L Lachman, JB Schwartz. "Pharmaceutical Dosage Forms: Tablets vol. 1." Second Edition, Revised and Expanded. Marcel Dekker Inc., 1989, pp. i-xviii and 1-592, 610 printed pages. (Year: 1989).*
X Li et al. "Discovery and development of pyrotinib: A novel irreversible EGFR/HER2 dual tyrosine kinase inhibitor with favorable safety profiles for the treatment of breast cancer." European Journal of Pharmaceutical Sciences, vol. 110, 2017, pp. 51-61. (Year: 2017).*
ChemScene. http://file.chemscene.com/EXCEL/CS-L001P.html accessed Aug. 30, 2019, 636 printed pages. (Year: 2019).*
The second method (paddle method) of the dissolution rate test disclosed in the appendix of vol. II of Chinese Pharmacopeia (2010 edition).
Int'l Search Report dated Apr. 28, 2017 in PCT Int'l Application No. PCT/CN2016/072156.
Modern Pharmaceutical Technology, vol. 2, Edited by Yingjin Yuan, published by Chemical Industry Press, 25 pages (2006) (Partial English Translation).
Pharmacopoeia of the People's Republic of China, Edition 2, Edited by National Pharmacopoeia Commission, Published by China Medical Science and Technology Press, 12 pages (2010) (Partial English Translation).

* cited by examiner

METHOD FOR PREPARING PHARMACEUTICAL COMPOSITION COMPRISING QUINOLINE DERIVATIVE OR SALT THEREOF

CROSS-REFERENCE TO RELATED APPLICATION

This application is a Section 371 of International Application No. PCT/CN2017/072156, filed Jan. 23, 2017, which was published in the Chinese language on Aug. 3, 2017, under International Publication No. WO 2017/129088 A1, which claims priority under 35 U.S.C. § 119(b) to Chinese Application No. 201610057228.3, filed Jan. 27, 2016, the disclosures of which are incorporated herein by reference in their entirety.

FIELD OF THE INVENTION

The present invention belongs to the field of pharmaceutical formulations, and specifically relates to a method for preparing a pharmaceutical composition comprising an active ingredient with chemical name (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide, or a pharmacologically acceptable salt thereof, and at least one pharmaceutically acceptable excipient. During the preparation process of the pharmaceutical composition of the present invention, wet granulation is carried out using a wetting agent comprising at least one organic solvent. The pharmaceutical composition prepared by the method of the present invention has a uniform distribution of particle size during the preparation process, and a property of rapid and uniform dissolution.

BACKGROUND OF THE INVENTION

CN102471312B discloses a small molecule compound of (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide that has a structure shown as formula I.

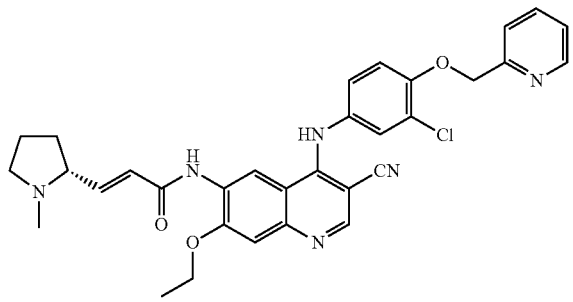

(I)

It is known as a small molecule receptor tyrosine kinase inhibitor that inhibits epidermal growth factor receptor (EGFR) and human epidermal factor receptor 2 (ERBB2). It can covalently bind to the ATP binding sites of the kinase domains of EGFR and ERBB2 in cells, prevent the formation of homogeneous and heterogeneous dimers of EGFR and ERBB2 in tumor cells, inhibit their own phosphorylation, and block the activation of downstream signaling pathway, thereby inhibiting the growth of tumor cells. It can be clinically used for the treatment of various tumors such as gastric cancer, lung cancer, and breast cancer, etc.

CN102933574B discloses a maleate salt form of the compound of formula I that has advantages in terms of solubility, bioavailability and pharmacokinetics in comparison to other salts and the compound of formula I itself.

CN103974949B discloses crystal form I of dimaleate salt of the compound of formula I. This crystal form has good crystalline stability and chemical stability, and can be used in the preparation of a medicament for treating diseases associated with EGFR receptor tyrosine kinase or HER-2 receptor tyrosine kinase.

However, when (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmaceutically acceptable salt thereof is prepared into a pharmaceutical solid composition, a high viscosity will be formed locally once the active ingredient is dissolved in water. It is not conducive to the preparation of the pharmaceutical formulation, and also causes the decline in drug dissolution rate and nonuniform dissolution rates of the pharmaceutical formulation in different individuals.

SUMMARY OF THE INVENTION

The object of the present invention is to provide a method for preparing a rapidly and uniformly dissolving pharmaceutical composition. The process for preparing the pharmaceutical composition is simple and is more suitable for large-scale production.

The present invention provides a method for preparing a pharmaceutical composition, comprising:
mixing the active ingredient (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide, or a pharmacologically acceptable salt thereof with a wetting agent, and granulating.

The pharmacologically acceptable salt can be hydrochloride salt, maleate salt, hydrobromide salt, p-toluenesulfonate salt, methanesulfonate salt, sulfate salt or ethanesulfonate salt, preferably maleate salt, and more preferably dimaleate salt. The active ingredient can be present in an amount of 5-70%, preferably 10-50%, and more preferably 20-40% by weight, relative to the total weight of the composition.

In the method for preparing a pharmaceutical composition according to the present invention, during the granulating process, the wetting agent can be finally removed by a drying process. The wetting agent can comprise at least one organic solvent, and can also comprise water, wherein the organic solvent can be an organic solvent with low toxicity, preferably ethanol and acetone, etc., and more preferably ethanol. The organic solvent can be present in an amount of 20-100%, preferably 50-95%, and more preferably 50-80% by weight, relative to the total weight of the wetting agent.

The method for preparing a pharmaceutical composition according to the present invention also comprises drying the resulting granules, and then tableting them into tablets or filling them into capsules to obtain oral solid formulations that are convenient for clinical administration.

In the method for preparing a pharmaceutical composition according to the present invention, the pharmaceutical composition can comprise one or more pharmaceutically acceptable excipient(s), for example a filler, a disintegrant, a binder, a lubricant, and the like.

The filler can be one or more of microcrystalline cellulose, calcium hydrogen phosphate, mannitol, pregelatinized starch, and lactose, etc. The filler is present in an amount of about 5-80% by weight, relative to the total weight of the composition.

The binder can be one or more of hydroxypropyl methyl cellulose, hydroxypropyl cellulose, sodium carboxymethyl cellulose, polyvinylpyrrolidone, and methyl cellulose, etc. The binder is present in an amount of about 0.5-15% by weight, relative to the total weight of the composition.

The disintegrant can be one or more of low-substituted hydroxypropyl cellulose, croscarmellose sodium, sodium carboxymethyl starch, and cross-linked polyvinylpyrrolidone, and preferably cross-linked polyvinylpyrrolidone. The disintegrant is present in an amount of 2-20%, preferably 4-15%, and more preferably 6-10% by weight, relative to the total weight of the composition.

The lubricant can be one or more of talc, magnesium stearate, zinc stearate, glyceryl behenate, sodium lauryl sulfate, hydrogenated vegetable oil, and colloidal silicon dioxide, etc. The lubricant is present in an amount of about 0.5-5% by weight, relative to the total weight of the composition.

In the method for preparing a pharmaceutical composition according to the present invention, one or more excipient(s) (for example the filler, disintegrant, and binder) can be mixed together with the wetting agent and active ingredient, followed by granulating and drying; or the granules obtained by mixing the active ingredient with the wetting agent are dried, followed by addition of one or more of excipient(s); or a part of the excipients can be mixed together with the active ingredient and wetting agent, and the other part is added after granulating and drying. Preferably, the filler, disintegrant, binder, active ingredient and wetting agent are mixed together followed by granulating and drying, then the lubricant is added.

The present invention also provides a method for preparing a pharmaceutical composition, comprising:

mixing the active ingredient (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide, or a pharmacologically acceptable salt thereof with a wetting agent, granulating, drying the resulting granules, and tableting them into tablets or filling them into capsules, wherein the wetting agent can be a mixed solvent of ethanol and water, the ethanol can be present in an amount of 50-80% by weight relative to the total weight of the wetting agent, and the pharmaceutical composition can also comprises:

1) 2-20 wt % of a disintegrant, wherein the disintegrant is cross-linked polyvinylpyrrolidone;

2) 5-80 wt % of a filler, wherein the filler is one or more selected from the group consisting of lactose and microcrystalline cellulose;

3) 0.5-15 wt % of a binder, wherein the binder is one or more selected from the group consisting of polyvinylpyrrolidone, hydroxypropyl methyl cellulose and hydroxypropyl cellulose; and 4) 0.5-5 wt % of a lubricant, wherein the lubricant is one or more selected from the group consisting of magnesium stearate and talc.

The content percentage of each component is based on the total weight of the pharmaceutical composition.

According to the method for preparing a pharmaceutical composition of the present invention, compared to pure water, the wetting agent comprising an organic solvent with low toxicity such as ethanol etc. is more ideal in the particle size distribution of the granules prepared by wet granulation. After the granules are prepared into an oral solid formulation, the dissolution of the active ingredient is more rapid, complete and uniform, which much more facilitates the drug to exert its efficacy.

The pharmaceutical composition obtained by the preparation method of the present invention dissolves rapidly and exerts its efficacy quickly, and can be used for the treatment of cancers such as gastric cancer, lung cancer or breast cancer, etc.

DETAILED DESCRIPTION OF THE INVENTION

The present invention will be further described in detail by the following examples and experimental examples. These examples and experimental examples are for illustrative purposes only and are not intended to limit the scope of the invention.

Examples 1-5, Comparative Example 1

The maleate salt of (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide (hereinafter referred to as compound A), lactose, microcrystalline cellulose, polyvinylpyrrolidone, and cross-linked polyvinylpyrrolidone were mixed in a ratio shown in Table 1. Wet granulation was carried out using an appropriate amount of purified water, 20 wt % ethanol solution in water, 50 wt % ethanol solution in water, 80 wt % ethanol solution in water, 93.75 wt % ethanol solution in water and anhydrous ethanol respectively as a wetting agent. The granules were dried until the moisture content was lower than 2%, and then dry milling was carried out. A prescription amount of magnesium stearate was added, and the mixture was mixed with a rotating mixer. 100 g of the resulting total mixed granules were separated for sieving, and the rest of the granules were tableted and coated to prepare tablets.

TABLE 1

| Components | Comparative Example 1 | Example 1 | Example 2 | Example 3 | Example 4 | Example 5 |
|---|---|---|---|---|---|---|
| Compound A | 31.1 | 31.1 | 31.1 | 31.1 | 31.1 | 31.1 |
| Lactose | 40.6 | 40.6 | 36.6 | 32.6 | 32.6 | 29.6 |
| Microcrystalline cellulose | 20.0 | 20.0 | 20.0 | 20.0 | 20.0 | 20.0 |
| Cross-linked polyvinylpyrrolidone | 8 | 8 | 8 | 8 | 8 | 8 |
| Polyvinylpyrrolidone | 3.3 | 3.3 | 3.3 | 3.3 | 3.3 | 3.3 |
| Magnesium stearate | 1.0 | 1.0 | 1.0 | 1.0 | 1.0 | 1.0 |
| Total | 100 | 100 | 100 | 100 | 100 | 100 |
| Wetting agent | Purified water | 20 wt % Ethanol | 50 wt % Ethanol | 80 wt % Ethanol | 93.75 wt % Ethanol | Anhydrous ethanol |

Unit: weight %

Experimental Example 1: Sieving Test 100 g of separated granules obtained in Examples 1-5 and Comparative Example 1 were shaken and sieved by using 50 mesh and 100 mesh screens. When purified water was used as a wetting agent in Comparative Example 1, there were a lot of large particles and fine powder in the resulting granules, and the particle size distribution was undesirable. When wetting agents comprising ethanol were used in Examples 1-5, there were less large particle and fine powder in the resulting granules, and the particle size distribution was more uniform.

Figure 1:
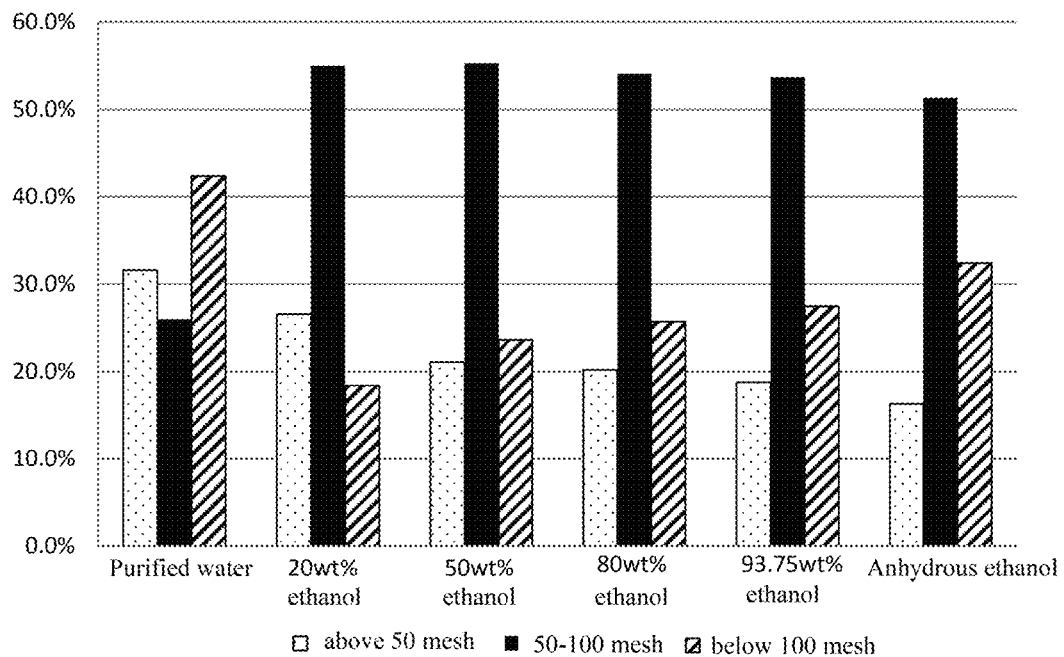
FIG. 1 shows the particle size distribution of the tablets of Examples 1-5 and Comparative Example 1.
Figure 2:
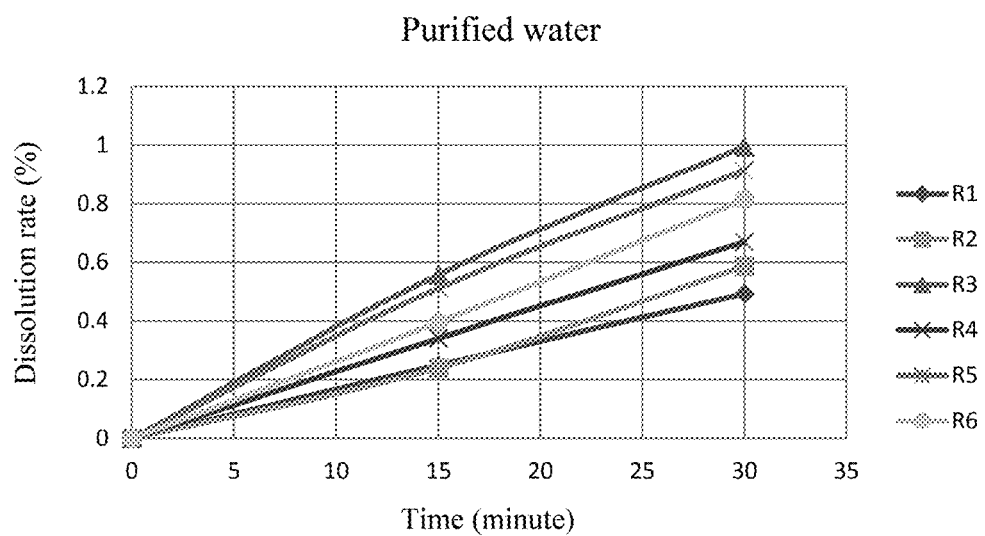
FIG. 2 shows the dissolution profiles of multiple tablet samples of Comparative Example 1 in a 0.1 mol/L hydrochloric acid solution.
Figure 3:
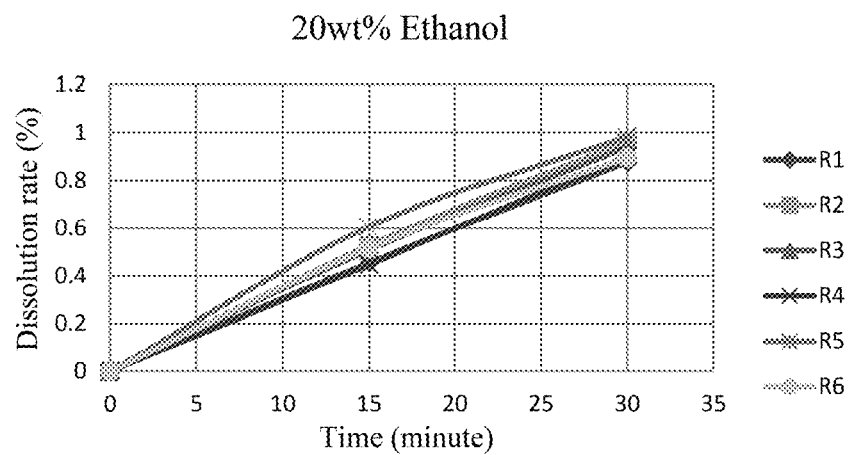
FIG. 3 shows the dissolution profiles of multiple tablet samples of Example 1 in a 0.1 mol/L hydrochloric acid solution.
Figure 4:
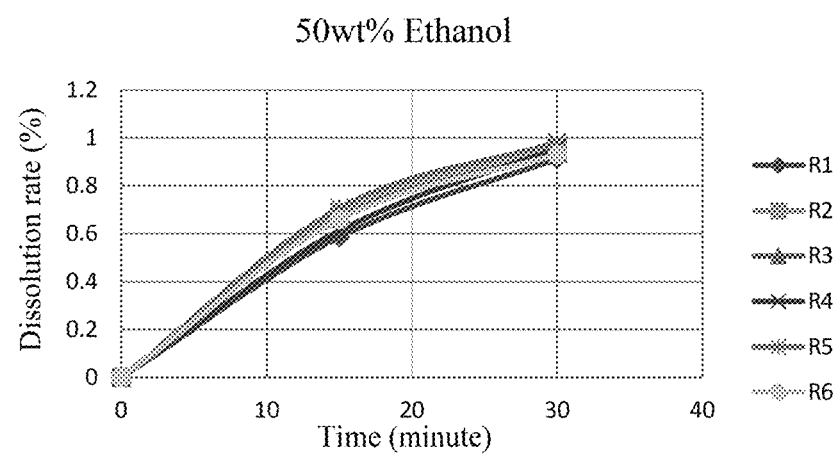
FIG. 4 shows the dissolution profiles of multiple tablet samples of Example 2 in a 0.1 mol/L hydrochloric acid solution.
Figure 5:
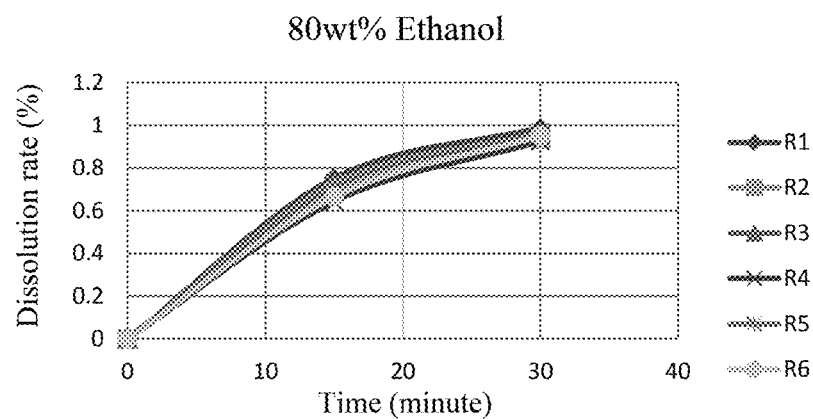
FIG. 5 shows the dissolution profiles of multiple tablet samples of Example 3 in a 0.1 mol/L hydrochloric acid solution.
Figure 6:
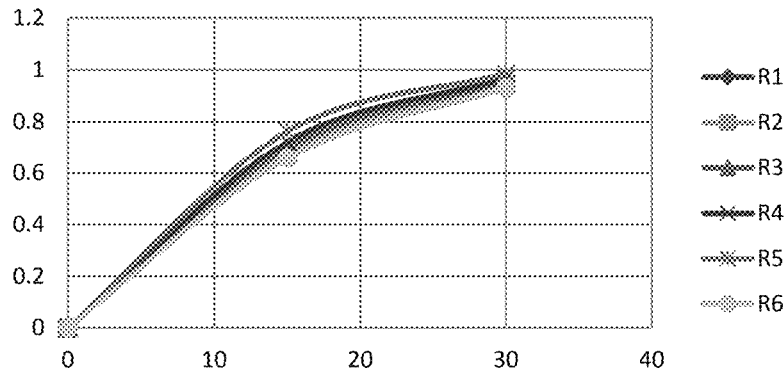
FIG. 6 shows the dissolution profiles of multiple tablet samples of Example 4 in a 0.1 mol/L hydrochloric acid solution.
Figure 7:
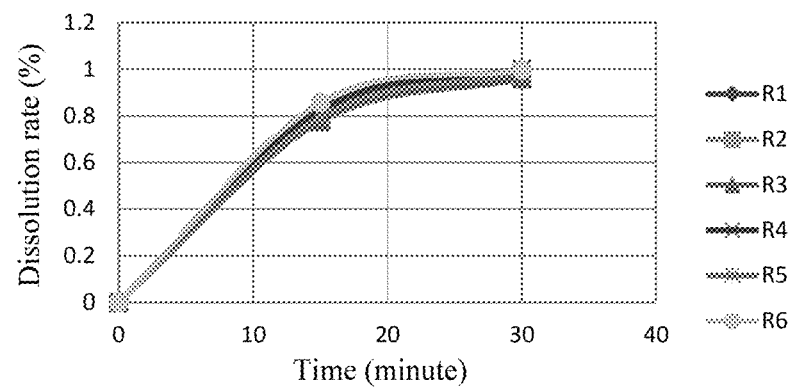
FIG. 7 shows the dissolution profiles of multiple tablet samples of Example 5 in a 0.1 mol/L hydrochloric acid solution.

The sieving results are shown in FIG. 1.

Experimental Example 2: Dissolution Test

The dissolution rates of the tablets of Examples 1-5 and Comparative Example 1 were determined according to the second method (paddle method) of the dissolution rate test disclosed in the appendix of volume II of Chinese Pharmacopeia (2010 edition). The dissolution test was carried out using 900 ml of 0.1 mol/L hydrochloric acid solution as a dissolution medium at 37±0.5° C. and at the paddle speed of 50 rpm. The results show that when 20 wt % ethanol aqueous solution, 50 wt % ethanol aqueous solution, 80 wt % ethanol aqueous solution, 93.75 wt % ethanol aqueous solution and anhydrous ethanol were used respectively as a wetting agent in Examples 1-5, the resulting granules had a desirable particle size distribution, and the dissolution of compound A was rapid and complete. When purified water was used as a wetting agent in Comparative Example 1, in the resulting tablets, the dissolution uniformity of compound A was poor. When wetting agents comprising ethanol were used as wetting agents in Examples 1-5, in the resulting tablets, the dissolution uniformity of compound A was good.

The dissolution profiles are shown in FIGS. 2-7, and the R1-R6 shown in the figures represent tested samples Tablet 1-Tablet 6.

Examples 6-11

Compound A, lactose, microcrystalline cellulose, polyvinylpyrrolidone, and cross-linked polyvinylpyrrolidone were mixed in a ratio shown in Table 2. Wet granulation was carried out using an appropriate amount of 93.75 wt % ethanol aqueous solution as a wetting agent. The granules were dried until the moisture content was lower than 2%, and then dry milling was carried out. A prescription amount of magnesium stearate was added, and the mixture was mixed with a rotating mixer. The resulting total mixed granules were tableted and coated to prepare tablets.

TABLE 2

| Components | Example 6 | Example 7 | Example 8 | Example 9 | Example 10 | Example 11 |
|---|---|---|---|---|---|---|
| Compound A | 31.1 | 31.1 | 31.1 | 31.1 | 15.5 | 46.6 |
| Lactose | 42.6 | 36.6 | 29.6 | 24.6 | 52.2 | 21.1 |
| Microcrystalline cellulose | 20.0 | 20.0 | 20.0 | 20.0 | 20.0 | 20.0 |
| Cross-linked polyvinylpyrrolidone | 2 | 8 | 15 | 20 | 8 | 8 |
| Polyvinylpyrrolidone | 3.3 | 3.3 | 3.3 | 3.3 | 3.3 | 3.3 |
| Magnesium stearate | 1.0 | 1.0 | 1.0 | 1.0 | 1.0 | 1.0 |
| Total | 100 | 100 | 100 | 100 | 100 | 100 |

Unit: % weight %

Experimental Example 3: Dissolution Test

The dissolution rates of the tablets of Examples 6-11 were determined according to the second method (paddle method) of the dissolution rate test disclosed in the appendix of volume II of Chinese Pharmacopeia (2010 edition). The dissolution test was carried out using 900 ml of 0.1 mol/L hydrochloric acid solution as a dissolution medium at 37±0.5° C. and at the paddle speed of 50 rpm. The results show that in the tablets of Examples 6-9 that comprise the disintegrant in different ratios and the tablets of Examples 10 and 11 that comprise compound A in different ratios, the dissolution of compound A was rapid and complete.

Figure 8:
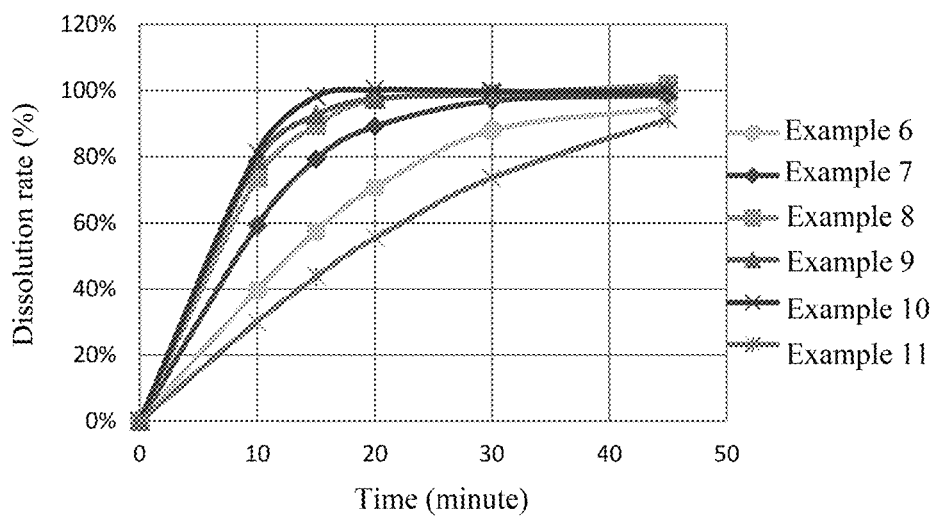
FIG. 8 shows the dissolution profiles of the tablets of Examples 6-11 in a 0.1 mol/L hydrochloric acid solution.

The dissolution profiles are shown in FIG. 8.

What is claimed is:

1. A method for preparing a pharmaceutical composition, comprising:
   (1) mixing the active ingredient (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide, or a pharmacologically acceptable salt thereof with a wetting agent and one or more additional ingredients to obtain a mixture,
   (2) granulating the mixture to obtain granules,
   (3) drying the granules to obtain dried granules, and
   (4) tableting the dried granules into tablets or filling dried granules into capsules to obtain the pharmaceutical composition, wherein:
the wetting agent is a mixed solvent of ethanol and water, the ethanol is present in an amount of 50-80% by weight relative to the total weight of the wetting agent, and
the pharmaceutical composition further comprises:
1) 2-20 wt % of a disintegrant, wherein the disintegrant is cross-linked polyvinylpyrrolidone;
2) 5-80 wt % of a filler, wherein the filler is one or more selected from the group consisting of lactose and microcrystalline cellulose;
3) 0.5-15 wt % of a binder, wherein the binder is one or more selected from the group consisting of polyvinylpyrrolidone, hydroxypropyl methyl cellulose and hydroxypropyl cellulose; and
4) 0.5-5 wt % of a lubricant, wherein the lubricant is one or more selected from the group consisting of magnesium stearate and talc,
wherein the pharmaceutical composition provides a dissolution rate such that at least 80% of the active ingredient is released from the pharmaceutical composition within 30 minutes when measured in a dissolution medium containing 0.1 mol/L hydrochloric acid solution at 37±0.5° C. and at a paddle speed of 50 rpm.

2. A pharmaceutical composition prepared by the method according to claim 1.

3. A method of preparing a tablet, comprising:
(1) mixing the following ingredients to obtain a first mixture:
(i) 10%-50 wt % of the active ingredient (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof;
(i) 2-20 wt % of a cross-linked polyvinylpyrrolidone;
(ii) 5-80 wt % of a filler comprising one or more agents selected from the group consisting of lactose and microcrystalline cellulose; and
(iii) 0.5-15 wt % of a binder comprising one or more agents selected from the group consisting of polyvinylpyrrolidone, hydroxypropyl methyl cellulose and hydroxypropyl cellulose;
(2) granulating the first mixture using a wetting agent to obtain wet granules, wherein the wetting agent contains a mixed solvent of ethanol and water, and ethanol is present in an amount of 50-95% by weight relative to the total weight of the wetting agent;
(3) drying the granules to obtain dried granules,
(4) mixing the dried granules with 0.5-5 wt % of a lubricant comprising one or more agent selected from the group consisting of magnesium stearate and talc to obtain a second mixture; and
(4) tableting the second mixture into the tablets.

4. A pharmaceutical composition prepared by the method according to claim 3.

* * * * *